(12) United States Patent
Giniger

(10) Patent No.: US 9,271,902 B2
(45) Date of Patent: Mar. 1, 2016

(54) WHITENING SYSTEM CAPABLE OF DELIVERING EFFECTIVE WHITENING ACTION

(76) Inventor: Martin S. Giniger, New York, NY (US)

( * ) Notice: Subject to any disclaimer, the term of this patent is extended or adjusted under 35 U.S.C. 154(b) by 2468 days.

(21) Appl. No.: 11/355,924

(22) Filed: Feb. 15, 2006

(65) Prior Publication Data

US 2006/0198803 A1     Sep. 7, 2006

Related U.S. Application Data

(60) Provisional application No. 60/653,421, filed on Feb. 15, 2005.

(51) Int. Cl.
*A61Q 11/00* (2006.01)
*A61K 8/22* (2006.01)
*A61K 8/72* (2006.01)
*A61K 8/04* (2006.01)

(52) U.S. Cl.
CPC . *A61K 8/046* (2013.01); *A61K 8/22* (2013.01); *A61Q 11/00* (2013.01); *A61K 2800/88* (2013.01)

(58) Field of Classification Search
USPC .............. 424/49, 58, 53; 433/215, 216, 217.1
See application file for complete search history.

(56) References Cited

U.S. PATENT DOCUMENTS

| | | | | | |
|---|---|---|---|---|---|
| 5,252,312 | A | * | 10/1993 | Gentile et al. | 424/44 |
| 5,560,862 | A | * | 10/1996 | Gosselink et al. | 252/186.39 |
| 5,665,332 | A | * | 9/1997 | Mundschenk et al. | 424/49 |
| 5,928,628 | A | * | 7/1999 | Pellico | 424/49 |
| 6,254,857 | B1 | * | 7/2001 | Hoic et al. | 424/53 |
| 2002/0006386 | A1 | * | 1/2002 | Ibsen et al. | 424/49 |
| 2006/0099156 | A1 | * | 5/2006 | MacDonald et al. | 424/53 |

* cited by examiner

*Primary Examiner* — Lezah Roberts
(74) *Attorney, Agent, or Firm* — Peter B. Scull; Hamilton DeSanctis & Cha LLP

(57) ABSTRACT

The invention provides a foamable composition for tooth bleaching which can be a one- or two-component system. The system has at least one peroxide compound, and at least one foaming agent. The composition can also contain at least one source of calcium, strontium and mixtures thereof, at least one de-sensitizing agent and at least one source of phosphate. The composition can produce a longer-lasting, collapsible foam structure with enhanced whitening action. The foamable composition can also be a one-component multi-phase system. A two-component composition can be packed in a two-compartment syringe. The syringe can also be fitted with a dispensing tip which may or may not have a static mixer.

18 Claims, 1 Drawing Sheet

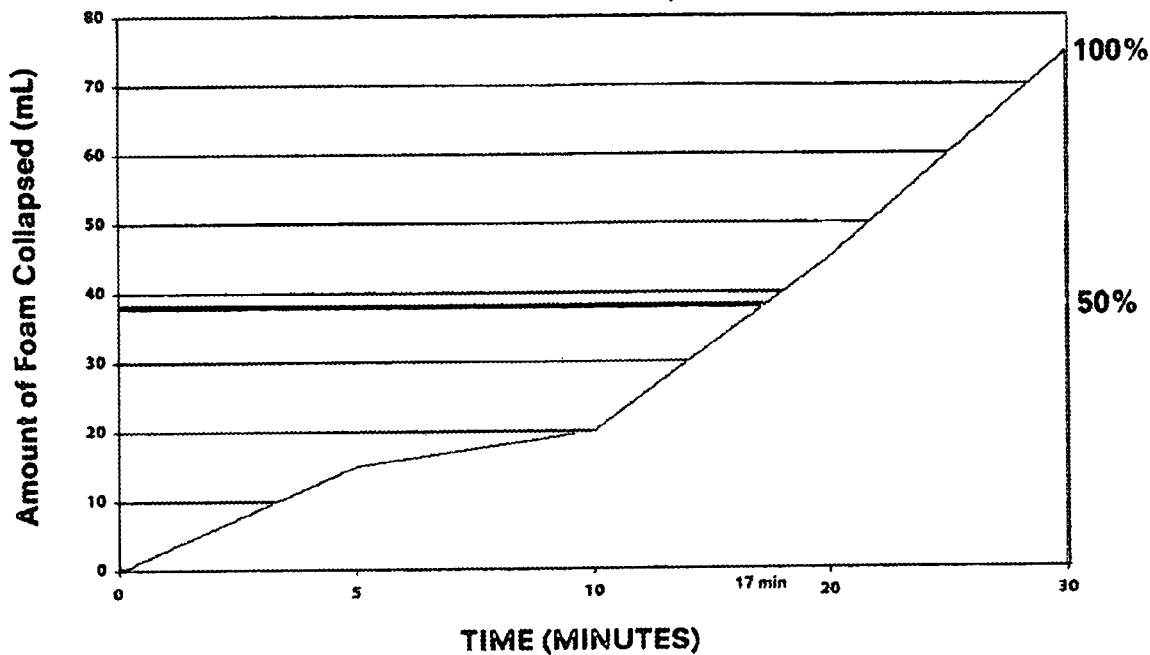

WHITENING SYSTEM CAPABLE OF DELIVERING EFFECTIVE WHITENING ACTION

CROSS-REFERENCE TO RELATED APPLICATIONS

The present invention claims the benefit of and priority from the prior-filed U.S. Provisional Patent Application, No. 60/653,421; filed Feb. 15, 2005, entitled "Whitening System Capable of Delivering Effective Whitening Action"; the subject matter of which hereby being specifically incorporated herein by reference for all that it discloses and teaches.

BACKGROUND

The present invention relates to improvements in tooth treatment compositions. In particular, this invention relates to whitening compositions in a form that is capable of delivering fast whitening action.

The coronal portion of the tooth consists of enamel, dentin and the pulp. In the mouth of humans, the enamel is coated with an acquired pellicle. The tooth structures that are generally responsible for presenting a stained appearance are enamel, dentin, and the acquired pellicle. Tooth enamel is predominantly formed from inorganic material, mostly in the form of hydroxyapatite crystals, and further contains approximately 5% organic material primarily in the form of collagen. In contrast, dentin is composed of about 20% protein including collagen, the balance consisting of inorganic material, predominantly hydroxyapatite crystals, similar to that found in enamel. The acquired pellicle is a proteinaceous layer or matrix that forms continuously over the surface of the tooth. Although the acquired pellicle can be removed through intensive mechanical cleaning, it quickly regenerates soon thereafter.

Discoloration of teeth can result from intrinsic and/or extrinsic staining. Intrinsic staining occurs when staining compounds penetrate the enamel and even the dentin, or alternatively, such staining arises from sources within the tooth. Typically such staining can only be removed through chemical methods of tooth cleaning. Some dentifrices, like toothpastes, gels, and powders, contain active oxygen or hydrogen peroxide liberating bleaching agents including peroxides, percarbonates and perborates of the alkali and alkaline earth metals or complex compounds containing hydrogen peroxide.

Commonly used dental bleaching agent include hydrogen peroxide, carbamide peroxide ($CO(NH_2)_2H_2O_2$), or urea hydrogen peroxide, hydrogen peroxide carbamide, and perhydrol-urea. Carbamides and hydrogen peroxides are used in over-the-counter compositions as well as bleaching gels are dispensed by dentists and commonly dispensed ones include those containing hydrogen peroxide (available as "Day-White" from Discus Dental, Inc.) and those containing a mixture of hydrogen peroxide and carbamide peroxide (available as "NiteWhite", also from Discus Dental, Inc.).

Some prior art discloses the use of concentrated carboxypolymethylene compositions for producing a matrix material having a sufficiently high viscosity, low solubility in saliva, and is sufficiently tacky to retain and hold a dental tray positioned over the patient's teeth for a period greater than about 2 hours without any significant mechanical pressure from the dental tray so as to provide for the dental bleaching agent to be in contact with the tooth surfaces thereby providing bleaching of the tooth surfaces.

The amount of whitening obtained during tooth bleaching is dependent upon (1) the length of time each day the tray is worn; (2) the number of days the tray is worn; (3) the susceptibility of the teeth to the bleaching agent and (4) the concentration of active peroxides. For maximum whitening, an accelerated treatment time of approximately 18-20 hours per day is recommended.

The prolonged period needed for effective bleaching can be time consuming. Thus, any whitening system that can potentially reduce the time factor is desirable.

SUMMARY OF THE INVENTION

The present invention relates to whitening compositions in a form that is capable of delivering faster whitening action.

The present invention comprises a 2-component foamable composition having a first component comprising at least one peroxide compound; and a second component comprising at least one foaming agent; wherein the two components combine to form a foam having a half life of from about 2 to about 60 minutes.

The present invention also comprises a 2-component foamable composition comprising a first component comprising at least one peroxide compound in an aqueous solution; and a second component comprising at least one foaming agent in solid form.

The present invention further comprises a one-component, multi-phase, foamable composition comprising at least one peroxide compound in an aqueous phase and at least one foaming agent in an oil phase, wherein the two phases combine to form a foam having a half life of from about 2 to about 60 minutes.

Still further, the present invention comprises a foamable one-component composition comprising at least one peroxide compound, wherein the resultant foam has a half life of from about 2 to about 60 minutes.

Furthermore, the present invention comprises a 2-component foamable composition having a first component comprising at least one peroxide compound in an aqueous solution and at least one peroxide stabilizer in the form of an ion scavenger; and a second component comprising at least one foaming agent and at least one peroxide activator; wherein said activator promotes the rapid decomposition of the peroxide compound and additional foaming action not related to the foaming agent.

Additionally, the present invention comprises a light-activatable, 2-component foamable composition having a first component comprising at least one peroxide compound; and a second component comprising at least one foaming agent and one lower oxidative state transition metal salt; wherein the two components combine to form a foam having a half life of from about 2 to about 60 minutes.

The present invention comprises yet a method of tooth bleaching comprising:
a. providing a whitening composition in a one- or two-component system, said composition comprising at least one peroxide compound and at least one foaming agent;
b. subjecting said whitening composition to a foaming action; and
c. applying said foam on a surface for bleaching.

The present invention comprises yet a method of tooth bleaching comprising:
a. providing a whitening composition in a two-component system, a first component comprises at least one peroxide compound and a second component comprises at least one foaming agent; and b. dispensing said first and second components through a manual dispenser to form a whitening foam.

The present invention comprises yet a method of tooth bleaching comprising:
a. providing a whitening composition in a two-component system, a first component comprises at least one peroxide compound and a second component comprises at least one foaming agent;
b. dispensing said first and second component through a manual dispenser to form a foam onto a surface for bleaching; and
c. illuminating the surface with light.

In one aspect, the foamable composition is substantially free of gelling agents, thickeners or other ingredients that will tend to inhibit foaming.

In another aspect, the foamable composition comprises ingredients capable of increasing the half life of the foam that is generated. The stabilizer is, for example, added to facilitate the formation of a water-soluble, longer-lasting, collapsible foam structure.

In a further aspect, the first component of the foamable composition comprises at least one source of calcium, strontium and mixtures thereof and the second component comprises at least one source of phosphate.

In yet a further aspect, the first component of the foamable composition also comprises a de-sensitizing agent.

In yet an additional aspect of the invention, the foamable composition comprises at least one peroxide activator.

In yet an additional aspect of the invention, the two-component foamable composition contains peroxide compounds in both components.

In yet an additional aspect of the invention, the foamable composition comprises foam stabilizers.

In yet an additional aspect of the invention, the foamable composition comprises peroxide activator.

In yet an additional aspect of the invention, the foamable composition comprises at least one solvent suitable for solubilizing stains.

In still yet another aspect of the invention, the two-component foamable composition is provided in a double-barrel syringe.

In still yet a further aspect of the invention, the two-component foamable composition is provided in a double-barrel pumpable dispenser. The pumpable dispenser can be provided with a metering device for varying the proportion of each component in the final foam. The metering device can be adjusted to produce ratios of the two components of about 10:1 to 1:10.

DETAIL DESCRIPTION OF THE INVENTION

The detailed description set forth below is intended as a description of the presently exemplified tooth bleaching composition provided in accordance with aspects of the present invention and is not intended to represent the only forms in which the present invention may be prepared or utilized. The description sets forth the features and the steps for preparing and using the tooth bleaching compositions of the present invention. It is to be understood, however, that the same or equivalent functions and ingredients incorporated in the tooth bleaching compositions may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

As used herein, a foaming agent includes an agent that can aid in foam generation, a mechanical foaming action, an agent capable of sustained foaming, an agent that generates a gas that produces foaming, an agent that helps a composition to become self-effervescent, or an agent that produces similar results.

Various means of whitening teeth are known. For example, the most common professionally applied chairside method comprises administering a light-activated gel under the supervision of a dentist using a protocol of three (3) twenty minute applications. Patients frequently become uncomfortable, agitated and/or bored during such a procedure that typically lasts 1.5 to 2 hours when all set-up and precautionary methods have been included. Also, because of the length of exposure to both the gel and the light, teeth and oral tissues can become irritated or experience a transient hypersensitivity reaction. Thus, any improvement that can result in decreased time, increased patient comfort and increase in bleaching efficiency is desirable.

A foamable whitening composition of the present invention is capable of delivering more efficient whitening action. The composition can be either a two-component system or a one-component, multi-phase system.

The composition comprises at least one peroxide component which, for example, comprises metal ion free peroxide compounds. Examples of suitable metal ion free peroxide compounds include hydrogen peroxide and organic peroxides including urea peroxide (carbamide peroxide), salts of peroxides formed from the alkali and alkaline earth metals, glyceryl peroxide, benzoyl peroxide and the like. Exemplified peroxides include hydrogen peroxide, carbamide peroxide, calcium peroxide and mixtures thereof, with a few of the examples being hydrogen peroxide or a mixture of hydrogen peroxide and carbamide peroxide. The total peroxide present in the foamable whitening composition, for example, ranges from about 1% by weight to about 45% by weight of the composition, further for example from about 5% by weight to about 35% by weight of the composition. Peroxide may also be present in both components of the composition.

When hydrogen peroxide is used, it is usually provided as a 50% aqueous solution. When used alone, the amount of the hydrogen peroxide aqueous solution in the first component ranges from, for example, about 2% to about 90% (1% to 45% in the absence of water), as noted above, further for example, the amount ranges from about 10% to about 60% (5% to 30% in the absence of water).

On the other hand, when carbamide peroxide is used, it is, for example, used in combination with hydrogen peroxide, though it can be used alone. When used in combination, the carbamide peroxide is generally present in an amount from, for example, about 0% by weight to about 40% by weight, and, further for example, in an amount from about 3% to about 35% by weight. At the same time, hydrogen peroxide, generally provided as a 50% aqueous solution, is present in an amount of from, for example, about 1% to about 30% (0.5% to 15% in the absence of water); further for example, in an amount of about 5% to about 30% (2.5% to 15% in the absence of water).

It is well established that peroxides such as hydrogen peroxide, carbamide peroxide, and salts of peroxides formed from the alkali and alkaline earth metals, readily attack and oxidize organic molecules that comprise the stains in discolored teeth. It is also well established that such oxidizing activity can be accelerated by the addition of heat, light and/or chemicals, specifically chemicals that can raise the pH of the peroxide environment. A possible dissertation of the exact mechanisms is discussed in prior work found in U.S. Pat. No. 6,116,900, "Binary energizer and peroxide delivery system for dental bleaching" which is herein incorporated by reference.

In addition to the addition of heat, light and/or chemicals, the amount of whitening obtained during tooth bleaching is generally dependent upon (1) the length of time the teeth is in contact with the whitening agent; (2) the number of days the treatment is carried out; (3) the susceptibility of the teeth to the bleaching agent; and (4) concentration of active peroxide, as noted above. For maximum whitening, a long treatment time with a highly concentrated bleaching composition is generally recommended.

Bleaching activity of a peroxide compound is generally dictated by the availability of active peroxides. When peroxide is present in solution, active peroxides are readily available. However, a solution, by its nature, is not easily contained, and/or not amenable for sustain action when applied to a patient's teeth, again because it is difficult to confine it to any desired location. Thus, a less concentrated peroxide solution requiring longer contact time to be effective is not practical, while a more concentrated solution of peroxide, though more efficient in bleaching, still does not solve the confinement problem, and any concentrated solution coming into contact with soft tissue inside a patient's mouth can potentially cause tissue damage. Therefore, to maintain effective bleaching without potential tissue damage, various gelling agents, thickeners and adhesion promoters are used to form paste, gels, and similar forms to achieve prolong contact effects. Unfortunately, such additives used to achieve prolong contact also help to decrease the bleaching activity of peroxides by inhibiting the availability of active peroxides. For example, bleaching gels usually contain thickeners derived from polymers of acrylic acid (carbomer), pyrrolidone analog thickeners, or others, all lead to diminish the whitening capacity of peroxides through ionic and covalent interactions within the gel, and thus act against the desired effect of tooth whitening.

A foamable composition of the present invention on the other hand, can solve the problems encountered by gels and the like. A foamed composition is manageable during use, is capable of delivering high concentration of peroxide without confinement problems, while at the same time will not seriously inhibit the availability of active peroxides. The foamed composition can also seek to fill crevices and gaps between enamel rods. Foam also has the ability to drain into and seep into gaps where gaps are not apparent, thus offering effective whitening action not only to the front surface of a tooth, but surfaces in-between teeth as well. A viscous composition that cannot flow between the enamel rods, and thickeners that inhibit the availability of active peroxides for tooth whitening, the present invention provides all the benefits not currently available to other whitening systems.

Aqueous solutions and gels without foaming action or surfactants tend to hold drops of water together as they try to become spherical, which is the reason why water tends to flow in tendrils rather than in sheets. At the atomic level, surface tension is seen as a macro effect of unbalanced electrical forces at the surface of the liquid, the same electrical forces that hold the molecules of the liquid together and keep it from evaporating. Within the body of a typical aqueous solution or gel, there are lots of molecules in all directions, and electrical forces are balanced on the average. A molecule is pulled equally in all directions by neighboring molecules, resulting in no net force on it. On the surface, however, there are only a scant few air molecules to counteract the pull of the liquid below. The result is an inward-directed force pulling on a molecule near the surface, ultimately forming an electrical armor that envelops the liquid like an ultra thin skin. Thus, it is easy to see that non-foaming bleaching gels tend to hold on to their active ingredients. Water molecules near the surface of gels intensify and magnify the surface tension, resulting in a so called "skin" effect by aligning to form a type of "elastic electrical force field" that seals and shields the surface even more. The shape of the water molecule leaves one of its ends with a slightly positive charge and the other end with slightly negative. Because of this electrical asymmetry (known as polarization), the negative and positive ends of adjacent molecules attract one another, creating a weak but significant physical bond. Energy is then required to stretch and break the bonds, and spreading out the liquid would mean that some of the bonds have to be broken. In this manner, most of the active peroxide molecules in a typical bleaching gel have difficulty escaping from the bondage to cause teeth whitening.

Foams in general have lower surface tension than their liquid solution counterparts prior to foaming and can therefore be spread as thin as one molecule thick sheets, while at the same time increasing its surface area. Thus, it is clear that the foamable composition of the present invention have advantages over gels and solutions. Without wishing to be bound to a theory, it is surmised that active peroxides can be captured inside the bubbles of foams. As the bubbles collapse, the active peroxide agent is released to perform whitening actions. Also, the foamed bubbles, through the forces of capillary action and lowered surface tension, are also wetting agents, a bleaching solution can penetrate through smaller openings by weakening the electrically charged "skin of surface tension" typically found in aqueous solutions and gels. The rapid penetration into the tightest spots is also aided by the distribution of bubble sizes and shapes. Thus, foams can cause deeper penetration of active peroxide molecules. Additionally, foaming agents increase the adhesion of a liquid to a solid surface by allowing it to spread over a greater surface area.

It is further surmised that aside from the ability to lower surface tension, foams can also act to propel the active peroxide molecules toward the teeth and also act as a molecular "Lint Roller" to grab stains and lift them off of tooth surfaces.

Thus, the composition comprises at least one foaming agent. Different categories of foaming agents are suitable, and they may produce foams in different ways. Suitable foaming agents can include certain surfactants such as anionic, nonionic, amphoteric, zwitterionic, cationic, and mixtures thereof.

Some of these many kinds of surfactants aid in foam formation and some do not. Some surfactants are useful purely for their foaming properties alone, some act only as emulsifiers or wetting agents without foaming, and some even act to reduce foaming.

Anionic surfactants include, but are not limited to water-soluble salts of alkyl sulfates having from 8 to 20 carbon atoms in the alkyl radical (e.g., sodium alkyl sulfate), water-soluble salts of sulfonated monoglycerides of fatty acids having from 8 to 20 carbon atoms and mixtures thereof. Examples of anionic surfactants include Sodium lauryl sulfate, sodium coconut monoglyceride sulfonates, phospholipids, sarcosinates, such as sodium lauryl sarcosinate, taurates, sodium lauryl sulfoacetate, sodium lauroyl isethionate, sodium laureth carboxylate, and sodium dodecyl benzenesulfonate. Many of these anionic surfactants are disclosed in U.S. Pat. No. 3,959,458, the content of which is incorporated herein in its entirety by reference.

Nonionic surfactants can include, but are not limited, to compounds comprising a hydrophilic and hydrophobic components (which maybe produced by the condensation of alkylene oxide groups (hydrophilic in nature) with an organic hydrophobic compound which may be aliphatic or alkyl-aromatic in nature). Examples of suitable nonionic surfactants include low viscosity poloxamers (under trade name Pluronic), low viscosity hydroxyethyl cellulose, polysorbates, polyoxyethylene sorbitan esters (under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures thereof.

Amphoteric surfactants can include, but are not limited to derivatives of aliphatic secondary and tertiary amines in which the aliphatic component can be a straight chain or branched and one of the aliphatic substituents contains from about 8 to about 18 carbon atoms and one contains an anionic water-solubilizing group, e.g., carboxylate, sulfonate, sulfate, phosphate, phosphonate, betaines, specifically cocamidopropyl betaine, and mixtures thereof. Many of these nonionic and amphoteric surfactants are disclosed in U.S. Pat. No. 4,051,234, the content of which is incorporated herein by reference in its entirety.

In the present invention, some of the surfactants used include, for example, those that not only have foaming capabilities, but also those with the ability to act as wetting agents.

Actually, any asymmetrical molecule dissolved in water will make at least a weak surfactant. Such weak surfactants may normally not be an effective foaming agent, but its effectiveness can be improved if a foaming dispenser is used. Asymmetrical molecules as used herein include those that contain a hydrophilic (water-loving) and a hydrophobic (water-fearing) segment. One end of the molecule is thus polar in nature and dissolves in water, while the other end is nonpolar in nature, avoids water and dissolves in oil and other nonpolar compounds. When in water, surfactant molecules aim their polar ends at the water molecules, leaving the nonpolar ends sticking out like little electromagnets to attract nonpolar molecules. It is surmised that in a foamable composition of the present invention, the polar ends eject active peroxide molecules like a rifle, and the non-polar ends lift tooth surface stain molecules like a chemical "lint roller" that loosens, breaks up and holds them onto the polar molecules, allowing them to be washed away with the water.

The amount of foaming agents can range, for example, from about 0.1% to about 5% by weight of the foamable composition, further for example, it can range from about 0.5% to about 3% by weight, and still further for example, it can be less than about 1% by weight.

Still other foaming agents can include reaction products of any effervescent compound with an acid. The effervescent compound is, for example, a pharmaceutically acceptable alkali metal carbonate or bicarbonate, such as sodium bicarbonate, potassium bicarbonate, sodium carbonate or potassium carbonate. The One of the examples is sodium bicarbonate. The amount used can range, for example, from about 1% to about 10% by weight, further for example, from about 3% to about 7%, still further for example, from about 3.5 to about 5.5% by weight of the composition. The amount used depends on the volume of foam required, the desired pH and the desired diffusional or proper osmotic activity of the foam to be formed.

Generally, the ratio of acid and effervescent compound ranges from, for example, about 1:0.5 to 1:25, further for example, from 1:1 to 1:4, by weight. Examples of suitable acids include water soluble carboxylic acids such as nitric, citric, lactic, tartaric, succinic, glycolic, malonic, oxalic, malic, fumaric, maleic, or acetic acid, and phosphoric acids. A few of the examples include 85% phosphoric acid, citric acid or tartaric acid, in an amount of from, for example, about 0.5% to about 5%, further for example, from about 1% to about 3% by weight of the composition.

Additionally, a foaming agent can also be a gaseous material. The gaseous material can be any inert gas or the gas can be generated by mixing a basic peroxide solution with an acid solution comprising a potassium salt such as potassium bromide or potassium chloride.

Since the whitening activity results when active peroxide comes into contact with the tooth, the foams generated, for example, are not too long lasting, but have a substantive body so that the amount of liquid formed, i.e., the collapsing of the foam bubbles to release active peroxide can be controlled and balanced. Therefore, the preferred compositions are not only foamable, but are also capable of producing longer lasting, collapsible foams.

The foams generally have half lives of, for example, from about 2 to 60 minutes, further for example, of at least about 5 to 30. A foam having a half life of 5 minutes means that 50% of the bubbles would collapse to release the encapsulated whitening agent, or that the volume of the foam is reduced by 50% in about 5 minutes after formation, and 75% of all the bubbles are gone, or the volume of the foam is reduced by 75% in about 10 minutes.

The collapse time or half lives of the foam depends on a number of factors. For example, the greater the amount of bubbles formed, the longer the collapse time. Also, the lower the viscosity of the stabilizer, the shorter the collapse time. The collapse time also depends on the nature of the other additives to the composition, which have surface active properties e.g., surfactants or preservatives.

The longer lasting foams can, for example, be generated by including a foam stabilizer in the composition. The foam stabilizer is, for example, a hydrogel-like mixture of gum and water. For example, the viscosity of a solution thickened with the stabilizer remains substantially the same in a wide pH range and is relatively independent of ionic strength and the thickener can be, for example, xanthan gum, hydroxyethyl cellulose having about 1000-5000 cps, or and thereof. The advantage of xanthan gum is that compositions containing it can have a low viscosity at high shear rates, and are thus relatively easy to pump, spray or spread. Xanthan gum also exhibits a high viscosity at low shear rates, thus preventing the composition from dripping or flowing into places where it is not wanted. Thus, in addition to good stabilization of foams, it also gives it the substantive body needed. Xanthan gum is also widely used in the food industry and thus is safe for consumption.

The stabilizer is, for example, used in such concentrations that solutions or dispersions containing it in its pre-swelled form have viscosities as measured by Rotational Viscometer CSR-10a of within the range of, for example, less than about 50 cps, further for example, less than about 20 cps, still further for example, less than about 10 cps. The concentration of stabilizers can range, for example, from about 0.1 to about 10%, further for example, from about 0.5 to about 5%, still further for example, less than about 1% by weight of the composition. When xanthan gum is used, it is, for example, present from about 0.5 to about 2% by weight of the composition. When hydroxyethyl cellulose is present, it is, for example, ranging from about 0.5 to about 2% by weight of the composition.

Surprisingly, the acidic compounds mentioned above, including tartaric, citric, nitric or phosphoric acid, if present, can also act as suitable stabilizers. The amount of acidic compound stabilizers, for example, ranges from about 0.1% to about 2% by weight of the composition.

For example, the time before 50% of the foam collapses is sufficiently long so that the teeth can be about 7 to about 8 shades lighter than their original tooth shade after three (3) applications of, for example, about 5 to about 10 minute duration when used in a photobleaching mode in a dental office setting. The advantage of the collapsibility of the foam formed by the composition of the present invention is that it collapses in a liquid of low viscosity, low surface tension and high ability to penetrate between teeth and between enamel rods, thus giving the bleaching composition the best opportunity to rapidly cause teeth whitening. On the other hand, the advantage of stable foams will insure that their adherence to teeth is better and thus will not running off or have to be constantly reapplied. Also the greater the volume of the foam, the higher the concentration of peroxide that can be used to cause rapid whitening of teeth without causing soft or hard tissue sensitivity issues. The ideal foam stability/collapsibility can also be easily adjusted according to customer desire.

For example, if present, any thickener also has a low viscosity so as not to inhibit the availability of active peroxides. The viscosity is generally, for example, less than about 1000 cps, further for example, less than about 500 cps, and further for example, less than about 100 cps and as fluid as less than 50 cps.

The second component in the two-component composition of the present invention can also comprise at least one foaming agent in solid form. The ingredients in solid form, for example can comprise Pluronic F68, Sodium Carbonate anhydrous, Sodium Bicarbonate, potassium iodide and mixtures thereof.

Further for example, foaming agents can comprise foamable surfactants including at least some difunctional block copolymer surfactant, such as those having terminal groups of primary hydroxyl groups, as well as those comprising a hydrophobic and a hydrophilic segment. Examples include Pluronic F68, Pluronic F88 and mixtures thereof.

As noted above, the composition of the present invention also comprises a single-component, multi-phase, foamable composition comprising at least one peroxide compound in an aqueous phase and at least one foaming agent in an oil phase. It is a well-known phenomenon that oil and water in general do not mix, and it is also a well-known phenomenon that they can be made to mix with the aid of foaming surfactants. Thus, upon mixing, the two-phases can combine to form a longer-lasting, collapsible foam. When a preferred surfactant is used, the surfactant emulsifies and disperses the liquid by lowering the surface tension of both oil and water in order to effectively mix them together. Examples of solid surfactants are also difunctional block copolymer surfactants, similar to those listed above, including those having terminal groups of primary hydroxyl groups, as well as those comprising a hydrophobic and a hydrophilic segment. Examples include Pluronic F68, Pluronic F88 and mixtures thereof.

As discussed above, substantivity, i.e. the ability of a product to linger, is a desirable property in any whitening composition. On the other hand when the desired property of a product is the ability to be rinsed off easily, a foaming surfactant would not be used. However, there is a desire in a whitening composition for both substantivity and the ability to be rinsed off easily. When this is needed, foams generated in a "foaming pump" can be used. Foaming pumps again can produce foams with all the desirable properties, while using a minimum of amount of surfactants, for example, of less than about 1.0%.

The composition of the present invention can also include other active ingredients, such as peroxide activators, de-sensitizing agents, re-mineralizing agents, and fluoridating agents.

The addition of peroxide activators can also increase the photobleaching efficiency of the foamable compositions of the present invention. Suitable peroxide activators comprises lower oxidative state transition metal salt. The metal salt catalyzes the bleaching action of the peroxide to produce faster effective bleaching at lower peroxide concentrations. The preferred transition metals are those of lower atomic numbers including lower atomic number transition metals such as those ranging from atomic number 21 to 30. Also, those with lower oxidative states are also more preferred, including Iron (II), manganese (II), cobalt (II), copper (II) and mixtures thereof, and most preferably Iron (II).

When used, only a very small amount of the transition metal salt is needed, for example, from about 0.01% by weight to about 4% by weight, further for example, from about 0.03% by weight to about 2% by weight, and even further for example, from about 0.04% to about 1% by weight.

The peroxide activator can also include alkali salts such as potassium iodide, potassium chloride, sodium iodine, sodium chloride and combinations thereof.

Even with improved efficiency and shorter treatment time, some patients may still experience sensitivity. Suitable desensitizing agents can include alkali nitrates such as potassium nitrate, sodium nitrate and lithium nitrate; and other potassium salts such as potassium chloride and potassium bicarbonate. Preferably, potassium nitrate is used. The percent of desensitizing agent can be present up to about, for example, 5 percent by weight, further for example, up to about 4 percent by weight, and even further for example, up to about 3 percent by weight.

Amorphous calcium compounds such as amorphous calcium phosphate (ACP), amorphous calcium phosphate fluoride (ACPF) and amorphous calcium carbonate phosphate (ACCP) amorphous calcium carbonate phosphate (ACCP), and amorphous calcium carbonate phosphate fluoride (ACCPF) can be used in remineralizing teeth. These amorphous compounds are disclosed in U.S. Pat. Nos. 5,037,639, 5,268, 167, 5,437,857, 5,562,895, 6,000,341, and 6,056,930, the disclosure of each is hereby incorporated by reference in its entirety.

In addition to amorphous calcium compounds, amorphous strontium compounds such as amorphous strontium phosphate (ASP), amorphous strontium phosphate fluoride (ASPF), amorphous strontium calcium phosphate (ASCP), amorphous strontium calcium carbonate phosphate (ASCCP), amorphous strontium carbonate phosphate fluoride (ASCPF) and amorphous strontium calcium carbonate phosphate fluoride (ASCCPF) for use in remineralization, as noted above. These compounds are disclosed in U.S. Pat. No. 5,534, 244, the content of which is hereby incorporated by reference in its entirety.

Some of the compounds above can also be used in fluoridating teeth. All of the above amorphous compounds or solutions which form the amorphous compounds, when applied either onto or into dental tissue prevent and/or repair dental weaknesses such as dental caries, exposed roots and dentin sensitivity.

For example, the first component of the whitening system comprises a source of phosphate and the second component comprises a source of calcium or strontium.

For example, the source of phosphate in the first component includes monosodium phosphate ($NAH_2PO_4$), disodium phosphate, tetrapotassium pyrophosphate and thereof. As discussed above, the second component, for example, comprises a source of calcium or strontium, which, when the two gel components are mixed, combines with phosphate to form the various amorphous calcium and/or strontium phosphates.

The source of phosphate is, for example, present in an amount of from about 0.2% to about 5% by weight, further for example, between about 0.2% to about 4% by weight.

The source of calcium, strontium or combinations thereof in the second component, for example, comprises a calcium salt, a strontium salt, and thereof, further for example, a calcium salt such as calcium nitrate, in an amount of from about 0.25% by weight to about 1.5% by weight, for example, about 0.3% to about 1% by weight.

When the two components are mixed, the source of phosphate and the source of calcium, strontium or mixture can combine to form calcium phosphate. When applied to the teeth, the calcium phosphate can precipitate onto the surface of the teeth where it may be incorporated into hydroxyapatite, assisting in remineralization of the tooth enamel, as discussed in U.S. Pat. Nos. 5,037,639, 5,268,167, 5,460,803, 5,534,244, 5,562,895, 6,000,341, and 6,056,930, noted above.

In practice, it is preferred to include as much phosphate as possible, as the phosphate salt further acts to adjust the pH of the first component. The pH of the system is from, for example, about 5 to about 8, further for example, from about 5.5 to about 6.5.

In addition, optional additives including emulsifiers, flavorings, coloring agents, anti-plaque agents, anti-staining compounds, excipients such as emollients, preservatives, other types of stabilizers such as antioxidants, chelating agents, tonicity modifiers (e.g. sodium chloride, manitol, sorbitol or glucose), spreading agents, pH adjusting agents and water soluble lubricants, e.g. propylene glycol, glycerol or polyethylene glycol. The concentration of each may easily be determined by a person skilled in the art.

Lecithin, a natural emulsifier found in soy and other plants, and gum arabic, which comes from the sap of certain species of acacia trees, can also be used as emulsifier, dispersant and wetting agents of the present invention.

Suitable preservatives include benzalkonium chloride, parabens, chlorhexidine acetate, chlorhexidine gluconate, sorbic acid, potassium sorbitol, chlorobutanol and phenoxyethanol.

For increasing peroxide stability during storage, a 3% disodium EDTA may be added to the peroxide component. Alternatively, stability may be enhanced by storing the product in a dark, cool, dry place or refrigerated. An acidic mixture also helps to stabilize the peroxide.

Suitable emollients are those used for topical applications e.g. di-n-octyl ether, fatty alcohol polyalkylene glycol ether, 2-ethylhexyl palmitate, and isopropyl fatty acid esters. The emollient, if used, is preferably dispersed in the same part as the stabilizer.

In packaging the tooth whitening composition of the present invention, any convenient means for effecting the separation of the two components before use can be utilized in addition to encapsulating the components in a multi-phase environment. For example, a single container can be compartmentalized so that the two components are housed in separate compartments and are dispensed simultaneously and admixed prior to application on the teeth. Alternatively, the two components can be contained in separate containers from which the respective phases are dispensed for admixture just prior to use. The containers can also comprise static mixers. An exemplary packaging is disclosed in U.S. Pat. Nos. 5,819,988, 6,065,645, 6,394,314, 6,564,972 and 6,698,622, incorporate herein by reference.

In one exemplary embodiment of the present invention, the two components are provided in separate chambers of a dual-barrel syringe. Immediately before use, the two components are mixed together in a, for example, 1:2 to a 5:1 ratio (first component to second component) by actuating the syringe, further for example, the gels are mixed in the 1:1 ratio. The admixed whitening gel is applied to the surface of the teeth directly from the syringe. Other combinations of the components are contemplated by the present invention, depending on the % variation of ingredients present in each component.

In addition, any of the dispensers can also be fitted with a metering device for varying the proportion of each component in the final foam. The metering device can be adjusted to produce ratios of the two components of about 10:1 to 1:10. The device can be in the form of a dispensing system features a measuring mechanism that connects to two separate, interlocking bottles. By rotating the dispenser head, a precise mixing ratio of blended ingredients can be attained. Specifically, a dispenser head comprises two pumps that offer varying proportions of volumetric dispensing that can be individually actuated in precise relationship to the positioning of the interior disc. This interior disc can be positioned precisely or locked into a specific ratio by rotating the dispenser head. The nozzle for metering dual dispenser pump bottle can either be a configuration in which both components are mixed with a static mixer incorporated within its tip or a two-opening configuration where the components are not mixed until application. The use of metering devices can result in improved manufacturing efficiency, as fewer concentrations need to be made and the final concentration can be easily adjusted.

BRIEF DESCRIPTION OF THE DRAWING

The FIGURE attached is an illustration of a measurement of foam collapse over time.

The present invention is further described by the following examples:

EXAMPLES

Example 1

Ingredients for making this exemplary composition according to the invention are set out in Table 1 below. They were prepared as follows:

Component 1 (acidic) was prepared by dissolving 0.8 grams of Pluronic F68 in 10 ml of water, followed by the addition of 0.5 grams of Potassium Hydroxide and 0.8 grams detergent with stirring using a lab mixer at room temperature. Then the mixture was acidified by adding 3 milliliters of 10% nitric acid and 3 grams of tartaric acid w/stirring, at 500 rpm at room temperature. The entire solution was diluted to 100 ml by adding 80 milliliters of a 50% Superoxol solution (50% hydrogen peroxide), followed by addition of 1 gram of Potassium Nitrate and stirred until thinned to a creamy white color. Next, 1.5 grams of Eugenol was then added as an antibacterial agent, 2.0 milliliters of mint flavoring was added to give a pleasant smell, and 0.5 grams of Calcium Nitrate was also added. The mixture pH was checked. A pH range of about 1.5 to about 2.5 was obtained through adjusting with either a 10% nitric acid or potassium hydroxide. The entire mixture was agitated at room temperature under vacuum for 30 minutes. The resulting acidic low-viscosity solution (30 cps) was poured into the other 50 ml compartment of the two-chamber metering pump dispenser.

Component 2 (basic) was prepared by adding 0.10 grams of potassium hydroxide and 0.50 grams of potassium iodide to 50 milliliters of distilled water, followed by the addition of 0.8 grams of detergent and 0.8 grams of foam stabilizer with stirring using a stand mixer set at 750 rpm at room temperature until a homogenous light hydrogel was formed. Then 38 milliliters of 1% Calcium Peroxide suspension and 2 milliliters of glycerin were added and blended until the mixture thinned and appeared clear and smooth. Then 2 grams of sodium carbonate was slowly added, followed by slow addition of 3 grams of sodium phosphate dihydrate, 1 gram of sodium bicarbonate and 0.10 grams of Disodium Phosphate. For photo activation purposes, 1.25 milliliters of 3.33% ferrous gluconate solution was added while mixing at 200 rpm and then at 500 rpm. For aesthetic purposes, 1 ml of FD&C Green #2 was also added. The pH was checked and adjusted with Potassium Hydroxide to a pH range of 10.2 to 11.2. Finally more distilled water was added to bring the entire solution to 100 ml. To disperse and hydrate the stabilizer, and to degas any bubble formed, this component was agitated at room temperature under vacuum for 20 minutes. The resulting low viscosity solution (48 cps) was poured into one 50 ml chambers of one of the metering pump dispensers.

TABLE 1

| Ingredient | AMT | Chemical/IUPAC/ "real" name | Available From | Purpose |
|---|---|---|---|---|
| Component 1 | | | | |
| H20 | 50.00 mL | same | N/A | carrier/solvent |
| KI | 0.50 g | same | Spectrum Chemical | peroxide activator |
| KOH | 0.10 g | same | Spectrum Chemical | pH modifier |
| PLURONIC F68 | 0.80 g | poloxamer 188 | BASF | foamer |
| TYLOSE H4000* | 0.80 g | Hydroxyethyl cellulose | Clariant | thickener |
| 1% CaO2 Suspension | 40.00 mL | calcium peroxide suspended in water | Spectrum Chemical | peroxide source |
| Glycerin | 2.00 mL | same | Spectrum Chemical | humectant, carrier, viscosity modifier |
| Sodium Carbonate | 1.00 g | same | Spectrum Chemical | effervescent component |
| Sodium Phosphate Dihydrate | 1.50 g | same | Spectrum Chemical | pH buffer and phosphate source |
| Baking Soda | 2.00 g | sodium bicarbonate | Spectrum Chemical | effervescent component |
| DiSodium Phosphate Monohydrate | 0.50 g | same | Spectrum Chemical | pH buffer and phosphate source |
| FeGluconate | 1.25 mL | ferrous gluconate | Spectrum Chemical | peroxide photoactivator |
| FDC Green #2 | 1.0 mL | FD&C Green No. 2 | Warner Jenkins | colorant |
| Component 2 | | | | |
| H20 | 9.00 mL | same | N/A | carrier/solvent |
| PLURONIC F68 | 0.80 g | poloxamer 188 | BASF | foamer |
| KOH | 0.50 g | same | Spectrum Chemical | pH modifier |
| TYLOSE R4000* | 0.80 g | Hydroxyethyl cellulose | Clariant | thickener |
| HNO3 10% | 3.00 mL | same | Spectrum Chemical | pH modifier |
| Tartaric Acid | 1.0 g | same | Spectrum Chemical | foam stabilizer |
| 50% H2O2 | 80.00 mL | same | Atofina | peroxide source |
| KN03 | 1.00 g | same | Spectrum Chemical | stabilizer - sensitivity reliever |
| EUGENOL | 1.50 mL | same | Junbunzlauer | stabilizer - sensitivity reliever |
| MINT | 2.00 mL | distilled peppermint oil | S&S Flavors | flavor, scent and stabilizer |
| CaN03.(H2O)4 | 0.50 g | same | Spectrum Chemical | Calcium source |
| ethanol | 1.50 mL | same | Spectrum Chemical | solvent |
| KOH/HNO3 | QS to pH 2.0 | same | Spectrum Chemical | pH modifier |

The metering dial of the pump dispenser was set so that 50% of each component was dispensed simultaneously and mixed through a nozzle containing a static mixer into a 20 ml plastic weighed boat. The plunger was actuated 6 times for dispensing 5.0 milliliters into the weighed boat. Further mixing of both components occurred by swirling the mixture for about 5 to about 10 seconds with a small disposable dental nylon applicator brush within the plastic well. The foam produced was poured into a measuring cylinder. The volume of the expanded foam was measured and its collapse with time was monitored.

The test results are as follows:

Foam volume, collapse rate and pH 4 ml of each component was used and it took approximately 10 seconds to actuate the dispenser 10 times. A maximum volume of 75 ml was obtained 3 minutes after the last discharge. After 7 minutes, the volume had decreased to 35 ml, and after 10 minutes the volume had decreased to 20 ml. It took 30 minutes before the foam collapsed completely. An example of collapse rate is s shown in the FIGURE (found illustrated in the attached drawing sheet). The pH of the foam was 8.2.

The amount of fluid used above was 3 ml from each chamber (6.0 ml total), and the total number of strokes of actuator was 6. The volume expansion went from 6 ml to 75 ml.

Example 2

This was made in a similar way as Example 1, except with different ingredients, as shown in Table 2.

TABLE 2

| Component 1 100 mL (basic) | | Component 2 100 mL (acidic) | |
|---|---|---|---|
| Water - | 93 mL | Water - | 51 mL |
| Potassium Hydroxide - | 0.7 grams | Tartaric Acid - | 3.0 grams |
| Potassium Iodide - | 0.9 grams | Sodium Lauryl Sulfate - | 1 gram |
| Sodium Lauryl Sulfate - | 1.0 gram | DiSodium | 4 grams |

TABLE 2-continued

| Component 1 100 mL (basic) | | Component 2 100 mL (acidic) | |
| --- | --- | --- | --- |
| Sodium Bicarbonate - | 2.0 grams | EDTA - | |
| FD&C Blue #1 Solution | 1 mL | Superoxol 50% $H_2O_2$- | 40 mL |
| Xanthan Gum - | 1.0 gram | Xanthan Gum - | 1 gram |

Both plungers of the dual chamber dispenser were actuated at the same time to cause foaming. Mixing of components 1 and 2 occurred in the attached mixing tip. The foam produced was filled into a measuring cylinder. The volume of the expanded foam was measured and its collapse with time was monitored.

Results of Test Experiments

Foam Volume, Foam Collapse Rate and pH 4 ml of each component was used and it took 10 seconds to actuate the dispenser 10 times. A volume of 75 ml was obtained 5 seconds after the last discharge. After 5 minutes the volume had decreased to 60 ml, and after 10 minutes the volume had decreased to 55 ml. It took a half hour before the foam collapsed completely. The pH of the foam was 6.78.

Amount of fluid used: 4 ml from each chamber (8.0 ml total); Number of Stroke of Actuator: 10; Volume expansion: 8 ml→75 ml; Expansion multiple: 9.4×.

Example 3 was made in the same manner as Example 1, except with different ingredients, as shown in Table 3 below:

TABLE 3

| Ingredient | Amount | Chemical/IUPAC/ "real" name | Available From | Purpose |
| --- | --- | --- | --- | --- |
| Component 1 | | | | |
| H20 | 50.00 mL | same | N/A | carrier/solvent |
| KOH | 0.10 g | same | Spectrum Chemical | pH modifier |
| PLURONIC F68 | 0.80 g | poloxamer 188 | BASF | foamer |
| TYLOSE H4000* | 0.80 g | Hydroxyethyl cellulose | Clariant | thickener |
| 1% CaO2 Suspension | 40.00 mL | calcium peroxide suspended in water | Spectrum Chemical | peroxide source |
| Sodium Carbonate | 1.00 g | same | Spectrum Chemical | effervescent component |
| Baking Soda | 2.00 g | sodium bicarbonate | Spectrum Chemical | effervescent component |
| Component 2 | | | | |
| H20 | 9.00 mL | same | N/A | carrier/solvent |
| PLURONIC F68 | 0.80 g | poloxamer 188 | BASF | foamer |
| TYLOSE H4000* | 0.80 g | Hydroxyethyl cellulose | Clariant | thickener |
| 50% H2O2 | 80.00 mL | Same | Atofina | peroxide source |
| KOH/HNO3 | QS to pH 2.0 | Same | Spectrum Chemical | pH modifier |

Example 4 was made in a similar manner as Example 1, except for the different ingredients, as shown in Table 4 below:

TABLE 4

| Ingredient | Amount | Chemical/IUPAC/ "real" name | Available From | Purpose |
| --- | --- | --- | --- | --- |
| Component 1 | | | | |
| H20 | 50.00 mL | Same | N/A | carrier/solvent |
| KOH | 0.10 g | Same | Spectrum Chemical | pH modifier |
| PLURONIC F68 | 0.80 g | poloxamer 188 | BASF | foamer |
| Sodium Carbonate | 1.0 g | Same | Spectrum Chemical | effervescent component |
| Baking Soda | 2.00 g | Sodium bicarbonate | Spectrum Chemical | effervescent component |
| Component 2 | | | | |
| H20 | 9.00 mL | Same | N/A | carrier/solvent |
| PLURONIC F68 | 0.80 g | poloxamer 188 | BASF | foamer |
| 50% H2O2 | 80.00 mL | Same | Atofina | peroxide source |
| KOH/HNO3 | QS to pH 2.0 | Same | Spectrum Chemical | pH modifier |

Having described the invention with reference to accompanying illustrations and of the invention, it is contemplated that other changes can be made without departing spirit or scope of the invention as set forth in the appended claims

What is claimed is:

1. A liquid collapsible foam two-component tooth whitening composition comprising:
   a first liquid component comprising an acid including a tartaric acid and at least one peroxide compound, and at least one carrier; and
   a second liquid component comprising:
      an effervescent compound that includes a carbonate; and,
      at least one foaming agent;
         wherein the foaming agent includes hydroxyethyl cellulose; and
   either the first or second components further including: eugenol;
   wherein the first and second liquid components are structurally configured to be maintained separated before use and are configured to be combined with each other just prior to use to form a liquid collapsible foam, with gas generated therein, the collapsible foam having a half life of about 2 to about 30 minutes; wherein the liquid collapsible foam is configured to be applied to the surface of the teeth directly; and wherein the foam collapses into a liquid.

2. The liquid collapsible foam composition of claim 1 wherein said peroxide compound comprises metal ion free peroxide compounds.

3. The liquid collapsible foam composition of claim 1 wherein said peroxide compound is selected from the group consisting of hydrogen peroxide, urea peroxide (carbamide peroxide), calcium peroxide, glyceryl peroxide, benzoyl peroxide and mixtures thereof.

4. The liquid collapsible foam composition of claim 1 wherein the peroxide compound is present from about 1% by weight to about 45% by weight of the first component.

5. The liquid collapsible foam composition of claim 1 wherein the peroxide compound is present from about 5% by weight to about 35% by weight of the first component.

6. The liquid collapsible foam composition of claim 1 wherein said foaming agent further comprises one or more selected from the group consisting of surfactants, alkali metal carbonates and bicarbonates, gas and mixtures thereof.

7. The liquid collapsible foam composition of claim 6 wherein said surfactant comprises ionic and non-ionic surfactants.

8. The liquid collapsible foam composition of claim 7 wherein said surfactant is selected from the group consisting of sodium lauryl sulfate, phospholipids, low viscosity poloxamers, and polysorbates.

9. The liquid collapsible foam composition of claim 1 wherein said foaming agent comprises a hydrophilic and a hydrophobic component.

10. The liquid collapsible foam composition of claim 1 wherein said first component further comprises an acidic compound selected from the group consisting of water soluble carboxylic acids, nitric acid, phosphoric acids and mixtures thereof.

11. The liquid collapsible foam composition of claim 1 further comprising a foam stabilizer selected from group consisting of acidic compounds, xanthan gums, hydroxyethyl cellulose, low viscosity thickeners, and mixtures thereof.

12. The liquid collapsible foam composition of claim 1 further comprising an ingredient selected from the group consisting of peroxide stabilizers, emulsifiers, flavorings, coloring agents, anti-plaque agents, anti-staining compounds, emollients, preservatives, antioxidants, chelating agents, tonicity modifiers, spreading agents, alcohols, pH adjusting agents, water soluble lubricants, and mixtures thereof.

13. The liquid collapsible foam composition of claim 1 further comprising at least one source of phosphate in the first component and at least one source of calcium, strontium, or combinations thereof in the second component.

14. The liquid collapsible foam composition of claim 13 wherein the source of phosphate acts as a pH adjuster.

15. The liquid collapsible foam composition of claim 1 wherein said first component comprises at least one peroxide compound in an aqueous solution and at least one peroxide stabilizer in the form of an ion scavenger; said second component comprises at least one foaming agent and at least one peroxide activator, wherein said activator promotes the rapid decomposition of the peroxide compound and additional foaming action not related to the foaming agent.

16. A liquid collapsible foam multi-component composition comprising:
    at least one peroxide compound, and
    at least one carrier; and,
    at least one foaming agent;
        wherein the foaming agent includes:
            hydroxyethyl cellulose; and
    further including:
    tartaric acid
    an effervescent compound that includes a carbonate; and
    eugenol;
    wherein the peroxide compound with tartaric acid and the effervescent compound that includes a carbonate with the foaming agent are configured separated before use and are configured to be combined just prior to use to generate a collapsible foam with a gas generated therewithin and wherein the collapsible foam generated has a half life of about 2 to about 30 minutes; wherein the collapsible foam is applied to the surface of the teeth directly; and wherein the foam collapses into a liquid.

17. The liquid collapsible foam composition of claim 16 wherein a foam is generated through mechanical action.

18. The liquid collapsible foam composition of claim 16 wherein said carrier comprises an ingredient selected form the group consisting of an alcohol, a peroxide activator, a peroxide stabilizer, a foaming agent, a foam stabilizer, a peroxide stabilizer, an emulsifier, flavorings, a coloring agent, an anti-plaque agent, an anti-staining compound, emollients, a preservative, an antioxidant, a chelating agent, tonicity modifiers, a spreading agent, an alcohol, a pH adjusting agent, water soluble lubricants, and mixtures thereof.

* * * * *